United States Patent [19]

Seiler, Jr. et al.

[11] Patent Number: 4,550,447
[45] Date of Patent: Nov. 5, 1985

[54] VASCULAR GRAFT PROSTHESIS

[75] Inventors: Louis Seiler, Jr., Huntington Beach; Robert F. Rosenbluth, Laguna Niguel, both of Calif.

[73] Assignee: Shiley Incorporated, Irvine, Calif.

[21] Appl. No.: 520,027

[22] Filed: Aug. 3, 1983

[51] Int. Cl.⁴ .................... A61F 1/00; B29G 7/02
[52] U.S. Cl. .................... 623/1; 128/334 R; 264/288.8; 264/289.3; 264/DIG. 47; 138/153; 138/172
[58] Field of Search .................... 3/1, 1.4; 128/334 R; 264/127, 280, 284, 288.4, 288.8, 289.3, 296, 519, DIG. 47; 138/153, 172, 137, 124–126, DIG. 3; 424/15

[56] References Cited

U.S. PATENT DOCUMENTS

| | | | |
|---|---|---|---|
| 3,117,173 | 1/1964 | Adams | 264/288.8 |
| 3,184,369 | 5/1965 | Haseley | 264/288.8 |
| 3,272,204 | 9/1966 | Artandi et al. | 128/334 |
| 3,304,557 | 2/1967 | Polansky | 3/1 |
| 3,479,670 | 11/1969 | Medell | 3/1 |
| 3,513,110 | 5/1970 | Noether | 260/2.5 |
| 3,642,967 | 2/1972 | Doll | 264/288.8 |
| 3,843,761 | 10/1974 | Bierenbaum et al. | 264/210 R |
| 3,953,566 | 4/1976 | Gore | 264/288 |
| 3,962,153 | 6/1976 | Gore | 260/2.5 R |
| 4,082,893 | 4/1978 | Okita | 428/376 |
| 4,208,745 | 6/1980 | Okita | 3/1.4 |
| 4,234,535 | 11/1980 | Okita | 264/519 |
| 4,304,010 | 12/1981 | Mano | 3/1.4 |
| 4,306,318 | 12/1981 | Mano et al. | 3/1.4 |
| 4,332,035 | 6/1982 | Mano | 3/1.4 |

FOREIGN PATENT DOCUMENTS 42-13560  8/1967  Japan .

Primary Examiner—Richard J. Apley
Assistant Examiner—Greg Beaucage
Attorney, Agent, or Firm—Charles J. Knuth; Peter C. Richardson; Allen Bloom

[57] ABSTRACT

A porous tube suitable for use as a vascular graft prosthesis is disclosed. It is reinforced by external ribs, integral with the tube wall. These ribs are generally transverse to the tube axis and less porous than the wall. Suitable tubing can be made from polymers exhibiting a significant degree of crystallinity, preferably polytetrafluoroethylene. Methods for making these ribbed, porous tubes are also disclosed.

9 Claims, 5 Drawing Figures

VASCULAR GRAFT PROSTHESIS

FIELD OF THE INVENTION

This invention relates to the field of porous vascular graft prostheses. Specifically, it relates to vascular grafts reinforced by integral transverse ribs.

The ideal synthetic vascular graft prosthesis should be a chemically inert, non-carcinogenic, nonantigenic tube that will not be physically modified by body fluids and will resist mechanical deterioration. To be usable, the ideal vascular graft must be easily implantable by having good suture holding characteristics and by being conformable to fit the exact anatomical position without occlusive kinking or pinching from external pressure.

For many years, replacements for arteries and veins have been made from woven or knitted fabrics, and these grafts have proven very useful in many surgical procedures. However, they must be manufactured with great care to achieve a uniform porosity in the fabric wall. Also, they must be specially treated and corrugated to create a wall structure that will permit the graft to be bent without kinking and perhaps blocking blood flow.

Recently, vascular grafts have been made from polytetrafluoroethylene (PTFE) tubing that has been stretched to create a uniform porous structure. Processes to make such tubing are disclosed in U.S. Pat. Nos. 3,953,566 and 3,962,153. These tubes have relatively uniform porosity longitudinally as well as through the wall. Similar tubes, but with a porosity gradient across the wall can be made by the processes of U.S. Pat. Nos. 4,234,535 and 4,332,035. Both types of porous PTFE tubes can be satisfactory, but their resistance to kinking and their resistance to crushing after implantation could be improved. In U.S. Pat. No. 4,332,035, the outer surface has a random, irregular pattern.

SUMMARY OF THE INVENTION

It is a principal object of this invention to provide a vascular graft prosthesis made of porous polymer tubing which has an improved resistance to kinking when bent, and improved crush resistance over current PTFE grafts. It is a second object to provide methods for producing such tubing.

The principal object is achieved by a porous, flexible polymer tube with a pattern of closely spaced, generally transverse ribs having a regular, repeating pattern on the external surface of the tube wall. The ribs are formed as an integral part of the tube wall and typically have a height, in the radial direction, of about 40% of the tube wall thickness. The ribs are less porous than the wall, which makes them denser and tougher than the wall.

The closely spaced transverse ribs reinforce the wall in several ways. They inhibit tube collapse due to kinking when the tube is bent. In this respect, the ribs act much as do the transverse corrugations formed on fabric vascular grafts. The ribs also reinforce the tube against rupture from relatively high internal pressure compared to that outside. Further, the ribs, being an integral part of the tube wall, will increase the tube's resistance to collapse from external pressure.

The ribs also confer a good suture holding property to the tube. Close spacing of the ribs insures that any suture will always be adjacent to a rib. A rib will present an increased thickness to a suture and, being less porous than the tube wall and thus denser and tougher, add resistance against the suture being torn through the porous wall by excess tension.

The polymer from which a vascular graft tube is made must be body and blood compatible. Further, the graft tube wall should be porous to permit tissue ingrowth from the outside, and to nourish the neointima that forms on the inside surface. On the other hand, the wall must not be so porous as to continuously leak blood. A satisfactory porosity is characterized by a uniform distribution of pores of average diameter ranging from about 0.1–30.0 microns and a sufficient total pore volume to result in an apparent wall density of about 10–70% of the non-porous polymer density.

An advantageous type of porosity for vascular graft use has been found to be the microstructure of interconnected nodes and fibers that is created by rapid stretching of a suitable polymer at a temperature below its melting temperature. Suitable polymers will have a significant degree of crystallinity, at least 30% and preferably greater than 50%. PTFE, which is available at greater than 98% crystalline, is a particularly suitable polymer. It is chemically inert, is body and blood compatible, and can be stretched to achieve the desired porous microstructure. Typical procedures for creating microporous PTFE are disclosed in U.S. Pat. Nos. 3,953,566 and 3,962,153. Some other polymers capable of being stretched into the desired microstructure are nylon, polyester and polypropylene. U.S. Pat. No. 3,513,110 discloses methods for making the porous microstructure from nylon and polyester; No. 3,843,761 from polypropylene.

The second object of this invention, to provide methods for producing the desired ribbed porous tubing, can be achieved by two similar methods. The first method creates the ribs and the wall porosity primarily by the stretching of a polymer tube at a temperature below the polymer melting temperature. The second method creates ribs on a stretched polymer tube primarily by shrinkage of porous rib polymer.

In the first method, the starting tube can be either a polymer tube as formed or one already stretched to a lesser degree than finally desired. The external surface of the starting tube is scored by a series of generally transverse cuts that will result in a desired rib pattern. The scoring cuts extend only partway through the tube wall. The scored tube is rapidly stretched, which simultaneously creates porosity in the tube wall, expands the transverse scoring cuts to produce the rib pattern, and leaves the polymer between cuts, which polymer constitutes the ribs, relatively unstretched and therefore less porous and denser than that of the tube wall. The properties of the ribbed tube are set by heating at a temperature above the stretching temperature for a short period of time while restraining the tube wall from axial shrinkage. During heat setting, the porous polymer constituting the ribs will shrink, because it is isolated from the axial tension applied to the tube wall by the rib forming transverse cuts. This shrinkage will result in an even greater density difference between rib and tube wall.

In the second method, a tube already stretched to the desired porosity is scored by a series of generally transverse cuts that will result in a desired rib pattern. The scoring cuts extend only partway through the tube wall. The scored tube is then heat set while the tube wall is restrained from axial shrinkage. Separation and densification of the ribs occurs by shrinkage of the porous polymer between the scoring cuts during that heat set step. Alternately, some of the rib separation can be created by scoring cuts that actually remove polymer.

DESCRIPTION OF THE PREFERRED EMBODIMENTS

Ribbed tubes for conversion into vascular graft prostheses, according to this invention, can be made from those flexible polymeric materials capable of being sterilized and suitable for long term use in contact with blood within the human body. They particularly must have the property of becoming porous when stretched at temperatures less than their melting temperatures. The preferred polymer is highly crystalline PTFE (less than about 2% amorphous). However, ribbed tubes can be made from other polymers with significant crystallinity, such as nylon, polyester and polypropylene.

Useful vascular graft tubes will be cylindrical in form and range in size from about 1.0 mm to about 36 mm inside diameter, with wall thickness of about 0.5 mm to about 2.0 mm. The internal tube surfaces should be macroscopically smooth.

The external ribs of this invention can be made in several different regular, repeating patterns, but all patterns must provide closely spaced, generally transverse ribs. The spacing can range from about 10-100 ribs per inch and the rib height, in the radial direction, can vary from about 20-70% of the tube wall thickness. The ribs can be in the form of closely spaced annular rings, or a reticular mesh pattern in which the main rib orientation is transverse to the tube axis, but the preferred pattern is a helical spiral about the tube axis of about 33 turns per inch, with a rib thickness of about 40% of the tube wall thickness.

Figure 1A:
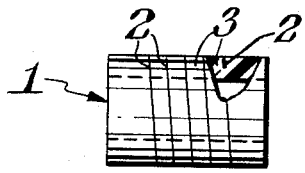
FIG. 1(a) shows a typical helical scoring of a tube wall.
Figure 1B:
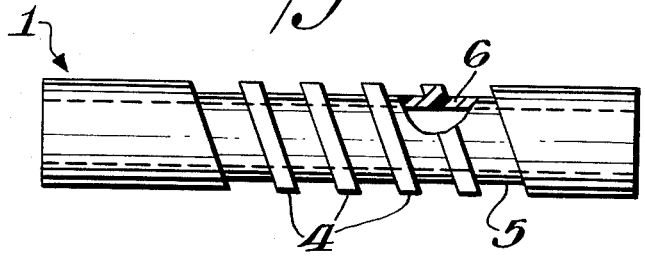
FIG. 1(b) shows the FIG. 1(a) tube after stretching.

FIG. 1(a) shows a side view of a portion of a tube 1 after scoring by knife cuts 2 in the preferred helical form to create potential ribs 3. FIG. 1(b) shows the same portion of the tube after a stretch in which the tube was elongated to about three times its starting length. Potential ribs 3 in FIG. 1(a) are now separated into actual ribs 4. This stretch has also exposed and external surface 5 of porous tube wall 6. The inner tube wall remains macroscopically smooth through out the successive operations.

Figure 2A:
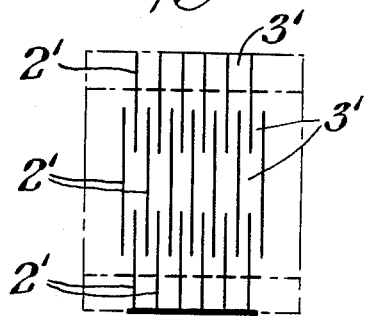
FIG. 2(a) shows a pattern of interrupted annular scoring cuts that will result in a reticular pattern of ribs.
Figure 2B:
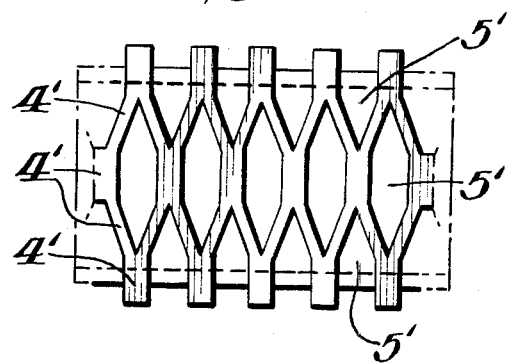
FIG. 2(b) shows the generally transverse reticular pattern of ribs created by the FIG. 2(a) scoring after stretching.

An alternative pattern of cuts is indicated in FIG. 2(a). It is a staggered series of interupted annular cuts 2' creating potential ribs 3'. After a stretching, FIG. 2(b) shows the resulting reticular pattern of generally transverse ribs 4', with the exposed external surface 5' of the porous tube wall.

For the tube of this invention to be suitable for use as a vascular graft prosthesis, the tube wall must be porous enough to permit some tissue ingrowth and to allow diffusion through the wall to nourish the neo-intima on the internal tube surface. However, it must not be so porous that it continuously leaks blood. Also the porosity must be essentially uniform along the tube length. The acceptable degree of porosity is an average pore diameter of about 0.1-30.0 microns as measured by bubble point using denatured alcohol as the wetting fluid, ASTM Standard F316 (1976), and such a concentration of pores that the apparent porous wall density is from about 10-70% of the non-porous polymer density. The preferred porosity is an average pore size of about 5 micron and an apparent wall density of about 35% of the non-porous polymer density. This porosity can be achieved by a microstructure of interconnected nodes and fibers, produced by the rapid stretching of significantly crystalline polymers at a temperature above about 20° C. and below the polymer melting temperature.

Figure 3:
FIG. 3 is a photomicrograph of an axial cross-section of the wall of a PTFE tube according to an embodiment of this invention. It shows two ribs on the external surface of the tube wall.

FIG. 3 is a photomicrograph of a longitudinal crossection of one wall of a preferred tube made of PTFE. The tube wall thickness, not including a rib, is about 0.8 mm, and the ribs rise about 0.4 mm above the tube wall. The ribs are about 0.3 mm wide (in the axial direction) and spaced about 0.7 mm apart. The wall microstructure of interconnected nodes and fibers and the reduced porosity of the rib polymer are clearly shown.

This PTFE tube was made by the first (stretching) method of rib creation. That method is generally as follows. PTFE is formed into a tube by the known paste extrusion method, since it is not practical to melt extrude PTFE, and the extrusion aid removed. This tube is heated to a temperature of about 200°-320° C. The hot tube is rapidly stretched from a starting length $L_0$ to a first stretched length $L_1$ so that the ratio $L_1/L_0$ is about 2-10. The outside surface of the stretched tube is scored with a cut in the form of a helix around the tube axis. Scoring can be done at stretching temperature, or the tube can be cooled to a convenient temperature before scoring. The cut typically will extend only about half way through the tube wall. The scored tube is stretched a second time at about 200°-320° C. from a starting length $L_1$ to a final length $L_2$, so that $L_2/L_1$ will be no more than about 6. The overall stretch ($L_2/L_0$) is the most important determinant of tube wall porosity. That overall stretch is preferably about 4.5 for PTFE. The second stretch serves both to achieve a desired wall porosity and to separate the ribs at the cuts. The polymer in the ribs, being isolated from stretching tension by the closely spaced rib cuts, is not significantly expanded by the second stretch. Therefore, the ribs retain the porosity of the first stretch while the wall becomes more porous. The final step is a setting of the porosity properties of the tube by a heat treatment while the tube wall is restrained from axial shrinkage. For a porous PTFE tube the heat setting occurs after about 3-20 minutes at about 327°-450° C. During this heat setting, the polymer in the ribs, being relatively unrestrained by axial tension in the tube wall, will shrink and accentuate the porosity and density difference between rib and wall.

In the second (shrinkage) method of rib creation, the process is the same as described above, with a first stretch where $L_1/L_0$ is about 2-10, but the second stretch is not done. Shrinkage of the porous rib polymer during heat setting is relied upon to create rib separation and relative densification.

An alternative to the first (stretching) method is done by eliminating the first stretching. In that situation, the tube as formed is scored. All stretching is done after scoring, and the ratio of final length to starting length will range from about 2-10.

In the methods described above, the various stretching steps can be done in one stage or in multiple stages. Stretching can be batchwise, as by elongating a fixed length of tube, or continuously as by a passage of the tube from one roll to another operating at a higher peripheral speed. The axial stretching could also be accompanied by radial stretching as described in U.S. Pat. No. 4,332,035, Example 2. Also, the scoring cuts can be made by any means: e.g. knife, laser beam or chemical etching. In some cases the cuts could actually remove polymer and create a preliminary rib separation.

The preferred method of producing a PTFE tube suitable for vascular graft use is illustrated by the following examples.

EXAMPLE 1

Eighty-four parts by weight of DuPont's "Teflon 60" grade of PTFE powder, which has a melting point of about 327° C. and contains less than 2% amorphous material, was mixed with 16 parts by weight of petroleum naphtha as extrusion aid. This mixture was compacted at 3500 psig and extruded through a tube die to create a tube of 6 mm ID and 0.75 mm wall thickness. After the naptha has evaporated, this paste extruded tube was heated to 300° C., and then rapidly stretched axially to 2.5 times its original length ($L_1/L_0=2.5$) in about one second. The external surface of the once stretched tube was scored by a cut 50% through the tube wall. The cut was in the form of a helix about the tube axis, to create a potential rib 0.508 mm wide in the form of a helix of 50 turns per inch. The scored tube was again rapidly stretched at 315° C. to 1.5 times its length ($L_2/L_1=1.5$) in about one second. The twice stretched tube was heat set by heating the tube at 350° C. for 9 minutes during which the tube was restrained from shrinking length wise. After cooling to room temperature, the tube had ribs on its external surface in a helical pattern of about 33 turns per inch. Tube wall thickness (without a rib) was 0.43 mm. The ribs averaged 0.23 mm high measured in the radial direction. The longitudinal width of a rib had shrunk during the heat set to an average of 0.23 mm. The tube wall had a porous micro structure of polymer nodes, about 3-5 micron wide by 10-100 micron long, interconnected by a network of fibers about 10-20 micron long. The wall porosity was such that the apparent density was 0.67 gm/cc (reduced from about 2.00 gm/cc for non-porous PTFE), with a maximum pore size of 2.0 micron as measured by bubble point as described by ASTM Standard F316 (1976).

EXAMPLE 2

A 6 mm I.D by 0.75 mm wall PTFE tube was extruded as in Example 1. After the naphtha had evaporated from the extruded tube, the tube was heated to 250° C. and rapidly stretched to 4.375 times its original length ($L_1/L_0=4.375$). The external surface of the stretched tube was scored in a helical pattern having a pitch of 33 turns per inch. This tube was heat set by heating the tube at 350° C. for 9 minutes during which time the tube was restrained from shrinking lengthwise. After cooling to room temperature, the tube had ribs on its external surface in a helical pattern of about 33 turns per inch. The unscored tube wall-thickness was 0.5 mm, and the rib height was 0.2 mm. The final rib width was 0.2 mm. The pore size measured using the bubble point method was 5 microns. The microstructure of the tube formed by the above Example 2 gave a typical node and fiber configuration of nodes of 5 to 7 microns wide with 10 to 25 micron long fibers connecting the nodes. The apparent density of this graft was 0.6 gm/cc.

The ribbed tubes of this invention are not limited to those of cylindrical form or having a smooth internal surface. For example, if desired for special use, the starting polymer tube could be extruded in elliptical form, or with longitudinal ridges along the internal surface.

Ribbed bifurcated grafts can also be made according to this invention by forming tubes into the desired bifurcated design by known means. After scoring to create the potential ribs, the scored bifurcated tube is stretched to create the rib pattern and desired porosity. The ribbed, porous bifurcated tube is heat set as previously described for single tube grafts.

While the ribbed, porous tubes produced by the above methods will have the physical properties desired for use as a vascular graft prosthesis, they can not be used for that purpose without further processing. This further processing comprises having the ribbed porous tube cut to useable lengths, washed, sterilized and enclosed in protective packaging. These steps are all conventional and can be done in any convenient order.

The preferred and alternate embodiments discussed and exemplified above are presented only to illustrate the invention. Those skilled in the art will see that many variations of tube design, of starting polymer and of processing method can be made without departing from the spirit of this invention.

We claim:
1. A flexible, monolithic, polymer tube comprising:
   a porous tube wall having a microstructure of interconnected nodes and fibers, and
   a generally transverse regular, repeating pattern of external ribs on said wall, said ribs being an integral part of said wall and being less porous than said wall.
2. A vascular graft prosthesis comprising:
   a flexible, monolithic, polymer tube, said tube having a wall and a closely spaced, generally transverse regular, repeating pattern of ribs on the external surface of said wall,
   said wall, having a microstructure of interconnected nodes and fibers and having a porosity suitable for use as a vascular graft, and
   said ribs being an integral part of said wall and being less porous than said wall.
3. The vascular graft prosthesis of claim 2, wherein said polymer is polytetrafluoroethylene.
4. The vascular graft prosthesis of claim 3, wherein the internal surface of the tube is macroscopically smooth.
5. The vascular graft prosthesis of claim 4, wherein said ribs are about 20% to 70% as high as said tube wall is thick.
6. The vascular graft prosthesis of claim 5, wherein said ribs are spaced about 10-100 per linear inch of tube surface.
7. The vascular graft prosthesis of claim 6, wherein said ribs are in the form of a helix about the tube axis.
8. The vascular graft prosthesis of claim 6, wherein said ribs are annular in form.
9. The vascular graft prosthesis of claim 6, wherein said ribs are in a reticular pattern.

* * * * *